(12) United States Patent
Takahashi et al.

(10) Patent No.: US 7,091,188 B2
(45) Date of Patent: Aug. 15, 2006

(54) STABILIZATION OF AMRUBICIN HYDROCHLORIDE

(75) Inventors: Kazuhiko Takahashi, Takatsuki (JP); Koji Fujimoto, Kitakatsuragi-gun (JP); Yasuko Yamauchi, Toyonaka (JP); Takanori Okahashi, Nishinomiya (JP)

(73) Assignees: Sumitomo Chemical Company, Limited, Osaka (JP); Dainippon Sumitomo Pharma Co., Ltd., Osaka-fu (JP)

( * ) Notice: Subject to any disclaimer, the term of this patent is extended or adjusted under 35 U.S.C. 154(b) by 31 days.

(21) Appl. No.: 10/489,824

(22) PCT Filed: Oct. 22, 2002

(86) PCT No.: PCT/JP02/10915

§ 371 (c)(1),
(2), (4) Date: Mar. 17, 2004

(87) PCT Pub. No.: WO03/035660

PCT Pub. Date: May 1, 2003

(65) Prior Publication Data

US 2004/0249137 A1 Dec. 9, 2004

(30) Foreign Application Priority Data

Oct. 23, 2001 (JP) .............................. 2001-324591
Oct. 23, 2001 (JP) .............................. 2001-324596

(51) Int. Cl.
*A01N 43/04* (2006.01)
*C07H 15/24* (2006.01)

(52) U.S. Cl. ......................................... 514/34; 536/6.4

(58) Field of Classification Search ................... 514/34
See application file for complete search history.

(56) References Cited

U.S. PATENT DOCUMENTS 6,376,469 B1* 4/2002 Shimago et al. ............... 514/34

FOREIGN PATENT DOCUMENTS

| EP | 302729 | 2/1989 |
|---|---|---|
| JP | 03-5397 | 1/1991 |
| JP | 2975018 | 9/1999 |
| WO | 99/28331 | 6/1999 |

* cited by examiner

*Primary Examiner*—Christopher S. F. Low
*Assistant Examiner*—Shirley V. Gembeh
(74) *Attorney, Agent, or Firm*—Wenderoth, Lind & Ponack, L.L.P.

(57) ABSTRACT

A stabilized amrubicin hydrochloride composition which comprises 3 to 8 wt. % water and 92 to 97 wt. % amrubicin hydrochloride; and a method of storing amrubicin hydrochloride.

4 Claims, 1 Drawing Sheet

STABILIZATION OF AMRUBICIN HYDROCHLORIDE

This application is a U.S. national stage of International Application No. PCT/JP02/10915 filed Oct. 22, 2002.

TECHNICAL FIELD

The present invention relates to a composition of amrubicin hydrochloride which is useful for a cancer chemotherapy agent, and its stabilization and storage methods.

BACKGROUND ART (7S,9S)-9-Acetyl-9-amino-7-[(2-deoxy-β-D-erythro-pentapyranosyl)oxy]-7,8,9,10-tetrahydro-6,11-dihydroxy-5,12-nephthacenedione hydrochloride represented by the formula (1):

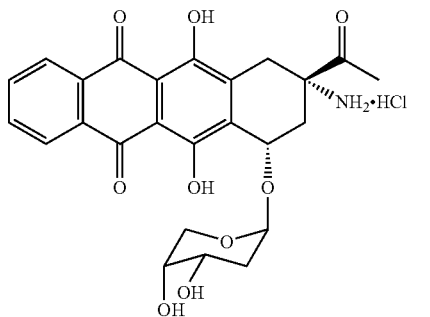

(1)

(hereinafter, referred to as amrubicin hydrochloride) has been known to be produced by, for example, the process described in JP 3-5397 B. In addition, amrubicin hydrochloride has been known to have several crystalline forms, a specific crystalline form of which is excellent in heat stability (JP 11-222497 A). However, sometimes, this compound generates as degradation by-products a desaccharification product represented by the formula (2):

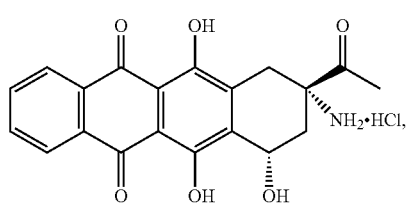

(2)

and a deamination product represented by the formula (3):

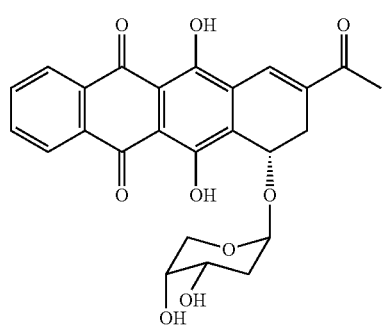

(3)

during handling thereof including drying, storage and transfer, though the amounts thereof are slight. In view of medical application, it is of very importance to further suppress the generation of these degradation by-products. In particular, since the deamination product forms insolubles during a production process of a pharmaceutical preparation, suppression of generation thereof is required more than that of the desaccharification product. In view of the above, it has been desired to further develop stabilization and storage methods.

DISCLOSURE OF THE INVENTION

An object of the present invention is to provide a stabilized composition of amrubicin hydrochloride, and stabilization and storage methods of amrubicin hydrochloride.

Thus, the present invention provides:
1. A stabilized amrubicin hydrochloride composition which comprises 92 to 97% by weight of amrubicin hydrochloride and 3 to 8% by weight of water;
2. A method for stabilizing amrubicin hydrochloride which comprises controlling a water content of amrubicin hydrochloride at 3 to 8% by weight; and
3. A method for storing amrubicin hydrochloride which comprises keeping amrubicin hydrochloride under an atmosphere at 5 to 90% relative humidity.

BEST MODE FOR PERFORMING THE INVENTION

Figure 1:
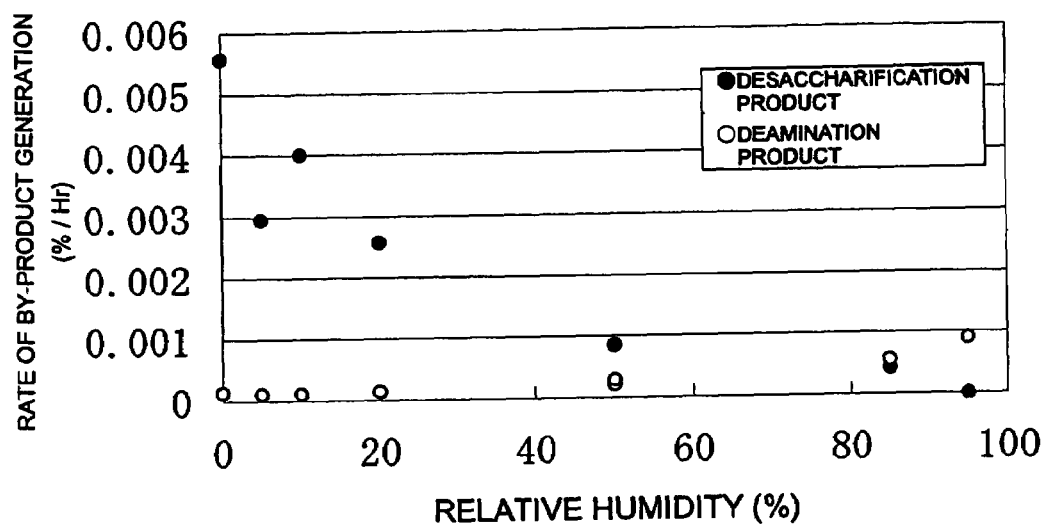
FIG. 1 is a graph prepared by plotting rates of by-product generation of the desaccharification product and the deamination product against relative humidity upon storage of amrubicin hydrochloride.

Amrubicin hydrochloride can be produced, for example, by the process described in JP 3-5397 B.

The by-product generation rates of the desaccharification product and the deamination product are influenced by a water content of amrubicin hydrochloride. The by-product generation rate of the desaccharification product is increased and the by-product generation rate of the deamination product is decreased according to the decrease in a water content of amrubicin hydrochloride. On the other hand, the by-product generation rate of the deamination product is increased and the by-product generation rate of the desaccharification product is decreased according to the increase in a water content of amrubicin hydrochloride. Then, in order to reduce the by-product generation rates of both desaccharification and deamination products to further stabilize amrubicin hydrochloride, it is of importance to control a water content of amrubicin hydrochloride at 3 to 8% by weight. In particular, in view of suppression of the by-product generation of the deamination product, more preferably, a water content of a composition of amrubicin hydrochloride is controlled at 4 to 7% by weight.

The water content is calculated by the following equation:

Water content (wt. %)=(weight of water contained in amrubicin hydrochloride)/(total weight of amrubicin hydrochloride including water)×100

The stabilized amrubicin hydrochloride composition comprising 92 to 97% by weight of amrubicin hydrochloride and 3 to 8% by weight of water can be obtained, for example, by such a method that dried amrubicin hydrochloride is exposed to wetted gas such as wetted air, wetted nitrogen, etc. to add a given amount of water thereto; that amrubicin hydrochloride wetted with water is dried under ordinary or reduced pressure, or with blowing drying gas such as nitrogen gas, etc. therethrough to adjust a water content of the amrubicin hydrochloride to 3 to 8% by weight; that gas for controlling moisture such as wetted nitrogen gas etc. is blown through dried or wetted amrubicin hydrochloride to adjust a water content of the amrubicin hydrochloride to 3 to 8% by weight; or the like. Usually, a water content of amrubicin hydrochloride can be adjusted to 3 to 8% by weight by exposing it to an atmosphere at 5 to 90% relative humidity. For bringing the water content to 3% by weight or higher, more preferably, the exposure is performed by adjusting the relative humidity to 10% or higher. For bringing the water content to 4% by weight or higher, more preferably, the exposure is performed by adjusting the relative humidity to 20% or higher. Further, for bringing the water content to 7% or lower, preferably, the exposure is performed by adjusting the relative humidity to preferably 85% or lower, more preferably 80% or lower, still more preferably 70% or lower. The relatively humidity can be set within the above range according to the desired water content. Usually, the relative humidity is adjusted to 5 to 90%, preferably 10 to 80%, more preferably 20 to 70%.

EXAMPLES

The following Example further illustrates the present invention in detail, but the present invention is not limited to the Example.

Example 1

Various compositions of amrubicin hydrochloride composed of about 91 to about 98% by weight of amrubicin hydrochloride and about 2 to about 9% by weight of water were prepared by exposing dried amrubicin hydrochloride to air whose relative humidity was adjusted (0 to 95%).

The thus-prepared amrubicin hydrochloride compositions having water contents of about 2 to about 9% by weight were stored at 30° C. and investigated rates of by-product generation of the degradation products, i.e., the desaccharification and deamination products.

The relative humidity was adjusted by reference to "Kobunshi Jikken-gaku Koza (Polymer Experiment Course) 5, Kobunshi no Bussei (Physical Properties of Polymers), 100–107 pages (Kyoritsu Shuppan Kabushiki Kaisha)".

FIG. 1 shows a graph prepared by plotting rates of by-product generation of the desaccharification and deamination products against the relative humidity of the storage atmosphere. It can be seen from this graph that the by-product generation of both desaccharification and deamination products can be suppressed by storing amrubicin hydrochloride under an atmosphere at 5 to 90% relative humidity, thereby permitting stable storage of amrubicin hydrochloride.

Figure 2:
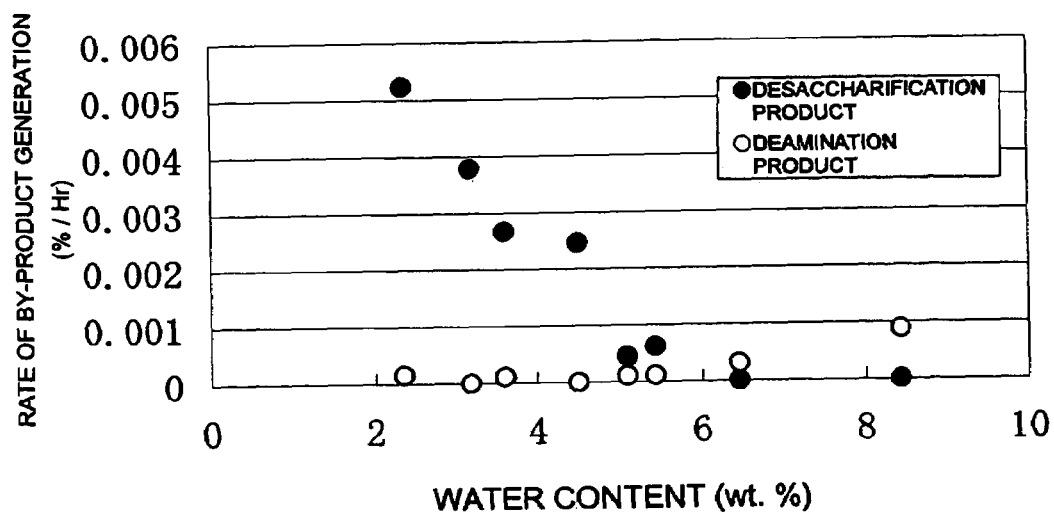
FIG. 2 is a graph prepared by plotting rates of by-product generation of the desaccharification product and the deamination product against water contents in compositions of amrubicin hydrochloride.

FIG. 2 shows a graph prepared by plotting rates of by-product generation the desaccharification product and the deamination product against water contents in compositions of amrubicin hydrochloride. It can be seen from this graph that the by-product generation of both desaccharification and deamination products can be suppressed by controlling a water content in an amrubicin hydrochloride composition at 3 to 8% by weight, thereby permitting stable storage of amrubicin hydrochloride.

INDUSTRIAL APPLICABILITY

According to the present invention, it is possible to stably store amrubicin hydrochloride by storing amrubicin hydrochloride under an atmosphere at 5 to 90% relative humidity to adjust a water content of amrubicin hydrochloride to 3 to 8% by weight, thereby suppressing the by-product generation of the desaccharification and deamination products.

The invention claimed is:

1. A stabilized amrubicin hydrochloride composition which comprises 92 to 97% by weight of amrubicin hydrochloride and 3 to 8% by weight of water.

2. The composition according to claim 1, wherein the water content is 4 to 7% by weight.

3. A method for stabilizing amrubicin hydrochloride which comprises controlling water content of amrubicin hydrochloride with gas for controlling moisture blown through dried or wetted amrubicin hydrochloride to adjust a water content of amrubicin hydrochloride to 3 to 8% by weight.

4. The method according to claim 3, wherein the water content is 4 to 7% by weight.

* * * * *